United States Patent
Zhu et al.

(10) Patent No.: US 11,617,526 B2
(45) Date of Patent: Apr. 4, 2023

(54) EMOTION INTERVENTION METHOD, DEVICE AND SYSTEM, AND COMPUTER-READABLE STORAGE MEDIUM AND HEALING ROOM

(71) Applicant: BOE TECHNOLOGY GROUP CO., LTD., Beijing (CN)

(72) Inventors: Hongwen Zhu, Beijing (CN); Zhihong Xu, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 246 days.

(21) Appl. No.: 16/758,743

(22) PCT Filed: Sep. 9, 2019

(86) PCT No.: PCT/CN2019/104911
§ 371 (c)(1),
(2) Date: Apr. 23, 2020

(87) PCT Pub. No.: WO2020/088102
PCT Pub. Date: May 7, 2020

(65) Prior Publication Data
US 2021/0219891 A1    Jul. 22, 2021

(30) Foreign Application Priority Data
Nov. 2, 2018    (CN) .......................... 201811303279.5

(51) Int. Cl.
*A61B 5/16*    (2006.01)
*G16H 20/70*    (2018.01)
*G06F 40/242*    (2020.01)
*A61B 5/00*    (2006.01)
*G06V 10/56*    (2022.01)
*G06V 40/16*    (2022.01)
(Continued)

(52) U.S. Cl.
CPC .............. *A61B 5/165* (2013.01); *A61B 5/486* (2013.01); *G06F 40/242* (2020.01); *G06F 40/284* (2020.01); *G06F 40/30* (2020.01); *G06V 10/56* (2022.01); *G06V 40/174* (2022.01); *G16H 20/70* (2018.01)

(58) Field of Classification Search
CPC ........ A61B 5/165; A61B 5/486; G16H 20/70; G06F 40/284; G06F 40/242; G06F 40/30; G06V 40/174; G06V 10/56
USPC ........................................................ 600/300
See application file for complete search history.

(56) References Cited

U.S. PATENT DOCUMENTS 9,098,114 B2 *    8/2015    Potter ................... G06F 3/0481
10,397,350 B2 *    8/2019    Goslin ................... G06V 40/70
(Continued)

FOREIGN PATENT DOCUMENTS

CN    101370195 A    2/2009
CN    102467668 A    5/2012
(Continued)

*Primary Examiner* — Zhen Y Wu
(74) *Attorney, Agent, or Firm* — The Webb Law Firm

(57) ABSTRACT

The present disclosure relates to a method, device, and system for emotion intervention, as well as a computer-readable storage medium and a healing room. The emotion intervention method includes: identifying a user's emotion state according to the user's first biometric information; and recommending at least one emotion intervention corresponding to the emotion state.

20 Claims, 9 Drawing Sheets

(51) Int. Cl.
  *G06F 40/284*  (2020.01)
  *G06F 40/30*  (2020.01)

(56) References Cited

U.S. PATENT DOCUMENTS

| | | | | |
|---|---|---|---|---|
| 2003/0212352 | A1* | 11/2003 | Kahn | A61H 1/008 601/103 |
| 2010/0325078 | A1* | 12/2010 | Lee | G16H 50/20 706/54 |
| 2011/0055720 | A1* | 3/2011 | Potter | G06F 3/0481 709/217 |
| 2011/0183305 | A1* | 7/2011 | Orbach | G09B 19/00 434/236 |
| 2012/0120219 | A1 | 5/2012 | Wang | |
| 2014/0223462 | A1* | 8/2014 | Aimone | G16H 40/67 725/10 |
| 2014/0244264 | A1* | 8/2014 | Thirumalainambi | G10L 25/63 704/270 |
| 2015/0053006 | A1* | 2/2015 | Decoux | G04D 7/001 73/579 |
| 2015/0053066 | A1* | 2/2015 | Hampiholi | G06V 20/597 84/602 |
| 2015/0169832 | A1* | 6/2015 | Davis | G06F 3/0346 702/19 |
| 2016/0063874 | A1 | 3/2016 | Czerwinski et al. | |
| 2017/0021282 | A1* | 1/2017 | Comploi | G05D 1/0088 |
| 2017/0064363 | A1* | 3/2017 | Wexler | H04N 5/23218 |
| 2017/0068994 | A1* | 3/2017 | Slomkowski | G06V 40/10 |
| 2017/0095192 | A1* | 4/2017 | Sadowsky | A61B 5/0205 |
| 2018/0032126 | A1* | 2/2018 | Liu | G06F 3/011 |
| 2018/0063064 | A1* | 3/2018 | Borse | H04L 67/06 |
| 2018/0174457 | A1* | 6/2018 | Taylor | G08G 1/096741 |
| 2018/0277145 | A1* | 9/2018 | Yamaya | G10L 15/22 |
| 2018/0325440 | A1 | 11/2018 | Wang | |
| 2020/0085673 | A1* | 3/2020 | Seo | A61H 9/0078 |
| 2020/0364457 | A1* | 11/2020 | Wang | G06Q 30/0282 |

FOREIGN PATENT DOCUMENTS

| | | |
|---|---|---|
| CN | 103164691 A | 6/2013 |
| CN | 103390060 A | 11/2013 |
| CN | 105354184 A | 2/2016 |
| CN | 105536118 A | 5/2016 |
| CN | 104220293 A | 9/2017 |
| CN | 108198607 A | 6/2018 |
| TW | 201220216 A1 | 5/2012 |

* cited by examiner

EMOTION INTERVENTION METHOD, DEVICE AND SYSTEM, AND COMPUTER-READABLE STORAGE MEDIUM AND HEALING ROOM

CROSS-REFERENCE TO RELATED APPLICATIONS

This application is the United States national phase of International Application No. PCT/CN2019/104911 and claims priority to Chinese Patent Application No. 201811303279.5, filed Nov. 2, 2018, the disclosures of which are hereby incorporated by reference in their entirety.

TECHNICAL FIELD

The present disclosure relates to the field of computer technology, and in particular, to a method, a device, and a system for emotion intervention, as well as a computer-readable storage medium and a healing room.

BACKGROUND

Human emotions play an important role in people's social interaction. With the rapid development of human-computer interaction technology, emotion computing has become one of the important research fields of artificial intelligence.

SUMMARY

According to a first aspect of the embodiments of the present disclosure, an emotion intervention method is provided, comprising: identifying an emotion state of a user according to first biometric information of the user; and recommending at least one emotion intervention way corresponding to the emotion state.

In some embodiments, at least one emotion intervention corresponding to the emotion state is recommended according to second biometric information of the user.

In some embodiments, recommending at least one emotion intervention way corresponding to the emotion state comprises: identifying a physical state of the user based on the second biometric information of the user; and recommending the at least one emotion intervention way corresponding to the emotion state according to the physical state of the user.

In some embodiments, the emotion intervention comprises at least one of output of media data, adjustment of ambient atmosphere, provision of diet, provision of psychological consultation, provision of emotion management courses, or physiotherapy.

In some embodiments, identifying an emotion state of the user comprises: obtaining first biometric information of the user in real time; determining real-time emotion states of the user based on the first biometric information obtained in real time; counting proportions of each of the real-time emotion states of the user in a unit time; and identifying a real-time emotion state with the largest proportion as the emotion state of the user in the unit time.

In some embodiments, obtaining first biometric information of the user comprises: obtaining an image of the user; identifying a face of the user from the image; identifying a facial expression of the user according to features of the face; and using the identified facial expression as the first biometric information.

In some embodiments, recommending at least one emotion intervention corresponding to the emotion state comprises: obtaining emotion intervention data corresponding to the emotion state of the user, the intervention data comprising at least one of a physiotherapy suggestion or media data; and recommending at least one emotion intervention way corresponding to the emotion state based on the obtained emotion intervention data.

In some embodiments, the emotion intervention method further comprises: annotating the obtained emotion intervention data; deleting emotion intervention data that do not match an objective of emotion intervention; and constructing an emotion intervention repository using the remaining emotion intervention data.

In some embodiments, the emotion intervention data are obtained by a text similarity matching algorithm.

In some embodiments, obtaining the emotion intervention data through a text similarity matching algorithm comprises: obtaining a keyword dictionary corresponding to an objective of emotion intervention, wherein the keyword dictionary comprises w keywords, where w is a positive integer; comparing the text similarity between the keyword dictionary and a text to be compared; and determining media data corresponding to the text with a text similarity exceeding a similarity threshold as the emotion intervention data.

In some embodiments, comparing the text similarity between the keyword dictionary and a text to be compared comprises: assigning weights to the keywords in the keyword dictionary and keywords in the text to be compared, respectively, wherein the weights reflect the importance of the keywords, and the keywords in the keyword dictionary have n weights, where n is a positive integer; performing an AND operation on the keywords in the keyword dictionary and the keywords in the text to be compared that have the same weights to obtain n keyword sets, wherein the n keyword sets comprise a keywords, where a is an integer; and computing a ratio of a and w to obtain a text similarity between the text to be compared and the keyword dictionary.

In some embodiments, the text to be compared is obtained by searching with keywords in the keyword dictionary.

In some embodiments, the first biometric information comprises at least one of a facial expression or a sound; and the second biometric information comprises at least one of a height, a weight, or a health condition.

In some embodiments, the emotion intervention method further comprises: determining whether a recommended emotion intervention way has been chosen by the user; and if a recommended emotion intervention has been chosen by the user, activating a corresponding emotion intervention.

In some embodiments, the emotion intervention method further comprises: according to a hue of a background color of a picture and/or an object comprised in the picture, determining a content conformance degree of the picture; and constructing a picture repository as an emotion intervention repository by using pictures having content conformance degrees greater than or equal to a first threshold.

In some embodiments, the emotion intervention method further comprises: searching for keywords matching a keyword dictionary A from the descriptive text of a picture, wherein the keyword dictionary A comprises $a_0$ keywords, $a_0$ being a positive integer, and the keywords matched in the keyword dictionary A forming a keyword dictionary $A_1$; performing similar word expansion on keywords in the keyword dictionary A to construct a keyword dictionary B; searching for keywords matching the keyword dictionary B from the descriptive text of the picture, wherein the keywords matched in the keyword dictionary B constitute a keyword dictionary $A_2$; from the descriptive text of the picture, searching for a sentence with a similar semantic to the keywords in the keyword dictionary B using a semantic analysis method, wherein keywords in the searched semantically similar sentence that match the keyword dictionary B constitute a keyword dictionary $A_3$; combining the keyword dictionaries $A_1$, $A_2$, and $A_3$ to constitute a keyword dictionary C, wherein the number of keywords in the keyword dictionary C that match the keyword dictionary A is c, where c is a positive integer; computing a keyword matching degree based on $a_0$ and c; and constructing a picture repository using pictures having keyword matching degrees greater than or equal to a second threshold, as an emotion intervention repository.

In some embodiments, the emotion intervention method further comprises: determining a larger value of the content matching degree and the keyword matching degree of the picture as the conformance degree of the picture; and constructing a picture repository as an emotion intervention repository using pictures that have conformance degrees greater than or equal to a third threshold.

According to a second aspect of the embodiments of the present disclosure, there is provided an emotion intervention device comprising: an identification unit configured to identify an emotion state of a user according to first biometric information of the user; and a recommendation unit configured to recommend at least one emotion intervention way corresponding to the emotion state.

According to a third aspect of the embodiments of the present disclosure, there is provided an emotion intervention device comprising: a memory; and a processor coupled to the memory, the processor configured to, based on instructions stored in the memory, carry out the emotion intervention method according to any one of the foregoing embodiments.

According to a fourth aspect of the embodiments of the present disclosure, there is provided a computer-readable storage medium having stored thereon a computer program that, when executed by a processor, implements the emotion intervention method according to any one of the foregoing embodiments.

According to a fifth aspect of the embodiments of the present disclosure, there is provided an emotion intervention system, comprising the emotion intervention device of any one of the foregoing embodiments.

In some embodiments, the emotion intervention system further comprises at least one of a physiotherapy device, an ambient atmosphere adjustment device, a display, a player, a diet provision module, a psychological consultation module, and an emotion management course module, wherein: the physiotherapy device is configured to, if the recommended emotion intervention comprises physiotherapy, perform physiotherapy on the user; the ambient atmosphere adjustment device is configured to, if the recommended emotion intervention comprises an ambient atmosphere adjustment, perform the ambient atmosphere adjustment; the display and the player are configured to, if the recommended emotion intervention comprises output of media data, output the media data; the diet provision module is configured to, if the recommended emotion intervention comprises provision of diet, provide a corresponding diet so as to stimulate the nervous system of the user from the sense of taste; the psychological consultation module is configured to, if the recommended emotion intervention comprises provision of psychological consultation, provide an online psychological consultation referral appointment service; the emotion management course module is configured to, if the recommended emotion intervention comprises provision of emotion management courses, provide emotion management courses such as online psychological management courses.

In some embodiments, the emotion intervention system further comprises at least one of an image sensor, a sound sensor, a measurement device, and an input device, wherein: the image sensor and the sound sensor are configured to obtain the first biometric information of user; and the measurement device and the input device are configured to obtain the second biometric information of the user.

In some embodiments, the physiotherapy device comprises a massage chair.

According to a sixth aspect of the embodiments of the present disclosure, there is provided a healing room, comprising the emotion intervention system of any one of the foregoing embodiments.

Other features and advantages of the present invention will become apparent from the following detailed description of exemplary embodiments of the present disclosure with reference to the accompanying drawings.

BRIEF DESCRIPTION OF THE DRAWINGS

The accompanying drawings, which are incorporated in and constitute a portion of this specification, illustrate embodiments of the present disclosure and, together with the description, serve to explain the principles of the present disclosure.

The present disclosure will be more clearly understood from the following detailed description with reference to the accompanying drawings.

Figure 1A:
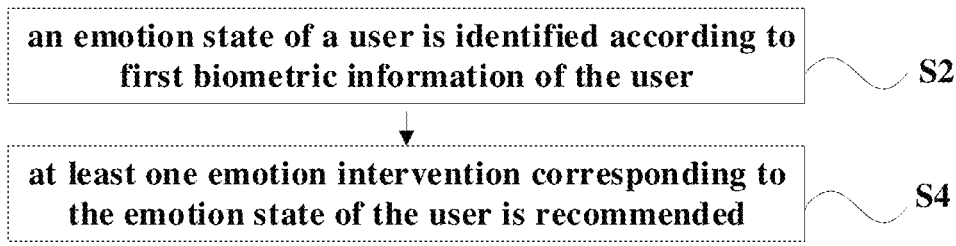
FIG. 1A is a flowchart illustrating an emotion intervention method according to an embodiment of the present disclosure.

It should be understood that the dimensions of the various parts shown in the drawings are not drawn to the actual scale. In addition, the same or similar reference signs are used to denote the same or similar components.

DETAILED DESCRIPTION

Various exemplary embodiments of the present disclosure will now be described in detail with reference to the accompanying drawings. The following description of the exemplary embodiments is in fact merely illustrative and is in no way intended as a limitation to the present disclosure, its application or use. The present disclosure may be implemented in many different forms, not limited to the embodiments described herein. These embodiments are provided so that this disclosure will be thorough and complete, and will fully convey the scope of the disclosure to those skilled in the art. Notice that, unless specifically stated otherwise, relative arrangement of components and steps set forth in these embodiments are to be construed as merely illustrative, and not as a limitation.

Unless otherwise defined, all terms (comprising technical and scientific terms) used herein have the same meaning as commonly understood by one of ordinary skill in the art to which exemplary embodiments in accordance with principles of inventive concepts belong. It will also be understood that terms defined in such general-purpose dictionaries should be interpreted as having a meaning that is consistent with their meaning in the context of the relevant art, and not to be interpreted in an idealized or overly formal sense, unless explicitly defined herein.

Techniques, methods, and apparatus known to those of ordinary skill in the relevant art may not be discussed in detail, but where appropriate, these techniques, methods, and apparatuses should be considered as part of the specification.

The present disclosure provides a scheme for emotion intervention based on emotion identification.

FIG. 1A is a flowchart illustrating an emotion intervention method according to an embodiment of the present disclosure. As shown in FIG. 1A, the emotion intervention method comprises steps S2 and S4.

In step S2, an emotion state of a user is identified according to first biometric information of the user.

The first biometric information comprises, for example, information capable of reflecting an emotion state such as a facial expression and a sound. The emotion state comprises, but is not limited to: neutral, happy, sad, angry, disdainful, disgusted, surprised, afraid. In some embodiments, emotion states can be divided into three types: neutral, positive, and negative. Happy can correspond to positive emotions. Sad, angry, disdainful, disgusted, surprised, afraid (or sadness, anger, contempt, disgust, surprise, fear) can correspond to negative emotions.

Figure 2:
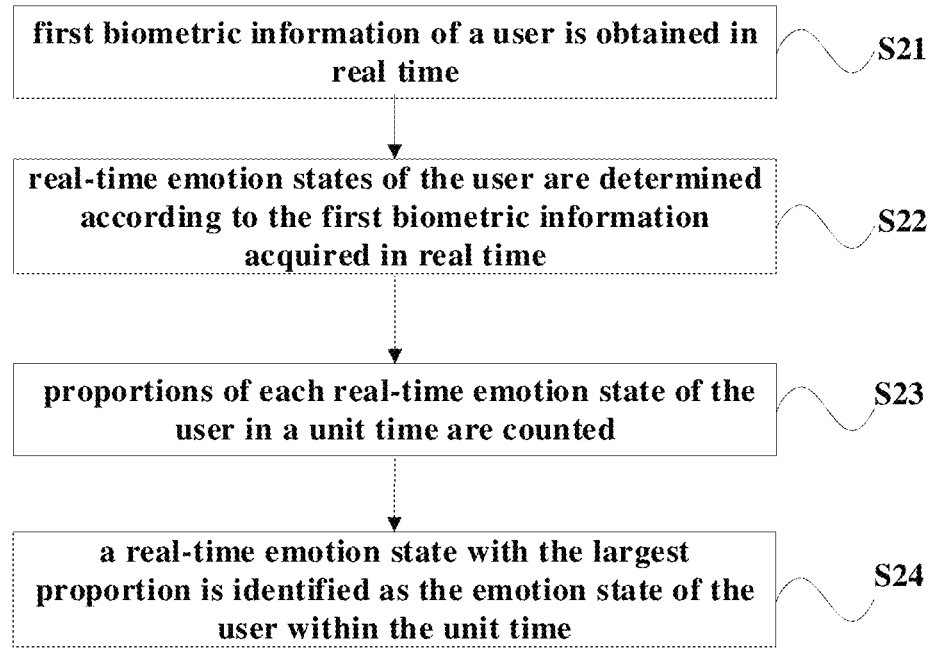
FIG. 2 is a flowchart illustrating an emotion identification method according to an embodiment of the present disclosure.

FIG. 2 is a flowchart illustrating an emotion identification method according to an embodiment of the present disclosure. As shown in FIG. 2, the emotion identification method comprises steps S21-S24.

In step S21, first biometric information of a user is obtained in real time.

In some embodiments, the first biometric information is obtained from an image of the user captured by an image sensor such as a camera. For example, a face is recognized from the user's image, and a facial expression of the user is identified as the first biometric information based on a correlation between facial features and expressions. Images of the user can be obtained periodically at regular time intervals.

In some embodiments, the image sensor may comprise a set of cameras. The set of cameras can be disposed in different orientations to obtain the user's images from multiple angles. For example, one camera can be disposed directly opposite to the user, and the remaining cameras can be separately disposed on both sides of the user. The angle between two adjacent cameras can be set to $180°/n_c$, where $n_c$ is the number of cameras.

Of course, the obtained user images can be compression-encoded to reduce the image size, thereby facilitating storage. It is also possible to record the time when a user image was captured, so that images from multiple angles captured at the same time can be stored in association.

In other embodiments, a sound of the user may also be sensed through a sound sensor such as a microphone as the first biometric information.

In step S22, a real-time emotion state of the user is determined according to the first biometric information acquired in real time.

Based on the correlation between emotions and biometric information such as facial expressions and sounds, a real-time emotion state of the user can be determined based on the information obtained in real time. For example, a pre-built emotion identification model can be used to classify different biological features into corresponding emotion states to establish a correlation between biological features and emotion states.

In step S23, a proportion of each real-time emotion state of the user in a unit time is counted.

In some embodiments, according to the number of occurrences of each real-time emotion state in a unit time, the proportion of each real-time emotion state of the user in the unit time is counted. For example, taking 2 seconds as a unit time, there are real-time emotion states that may appear. If the numbers of occurrences of different real-time emotion states in unit time are $n_i$, $1 \leq i \leq 8$ respectively, and the total number of occurrences of real-time emotion states is $$N = \sum_{i=1}^{8} n_i, 1 \leq i \leq 8,$$

the proportions of the various emotion states are $$P_i = \frac{n_i}{\sum_{i=1}^{8} n_i}, 1 \leq i \leq 8.$$

Assume that in a unit time of 2 seconds, only two real-time emotion states, i.e., Angry and Calm appear. Taking an example of obtaining information every 0.2 seconds, the counting result may be: 7 times of Angry and 3 times of Calm appear in 2 seconds, then $n_1=7$, $n_2=3$, $N=10$, $P_1=0.7$, $P_2=0.3$.

In step S24, a real-time emotion state with the largest proportion is identified as the emotion state of the user within the unit time. In the above example, Angry having a proportion of 0.7 is identified as the emotion state of the user within the unit time of 0.2 seconds.

In some embodiments, a user emotion report may be generated based on the identified emotion state.

Returning to FIG. 1A, how to recommend a corresponding emotion intervention after the user's emotion state is identified will be described below.

In step S4, at least one emotion intervention way corresponding to the emotion state of the user is recommended.

In some embodiments, corresponding emotion intervention data is obtained according to the emotion state of the user; based on the obtained emotion intervention data, at least one emotion intervention way corresponding to the emotion state is recommended.

The emotion intervention may comprise at least one of physiotherapy, output of media data, adjustment of ambient atmosphere, provision of diet, provision of psychological consultation, or provision of emotion management courses. Accordingly, the emotion intervention data may comprise at least one of corresponding data.

Physiotherapy can relate to different parts, such as eye physiotherapy, head physiotherapy, shoulder physiotherapy, neck physiotherapy, and leg physiotherapy. Physiotherapy methods comprise, for example, massage, light therapy, and magnetic therapy. Media data comprises pictures, audio, and video that can emotionally interfere with users. The emotion intervention data can comprise pictures, text, audio, and video in form.

The ambient atmosphere comprises light, negative oxygen ion, odor, etc. Psychological consultation is to, based on the user's emotion state, to evaluate the user's mental health using big data modeling, and to provide psychological self-referral appointment service to users whose evaluation results are at high risk of mental imbalance in order to provide emotional health management. Emotion management courses comprise, for example, parent-child courses, intimacy courses, emotion quotient courses, adversity quotient courses, social courses, and the like.

Figure 1B:
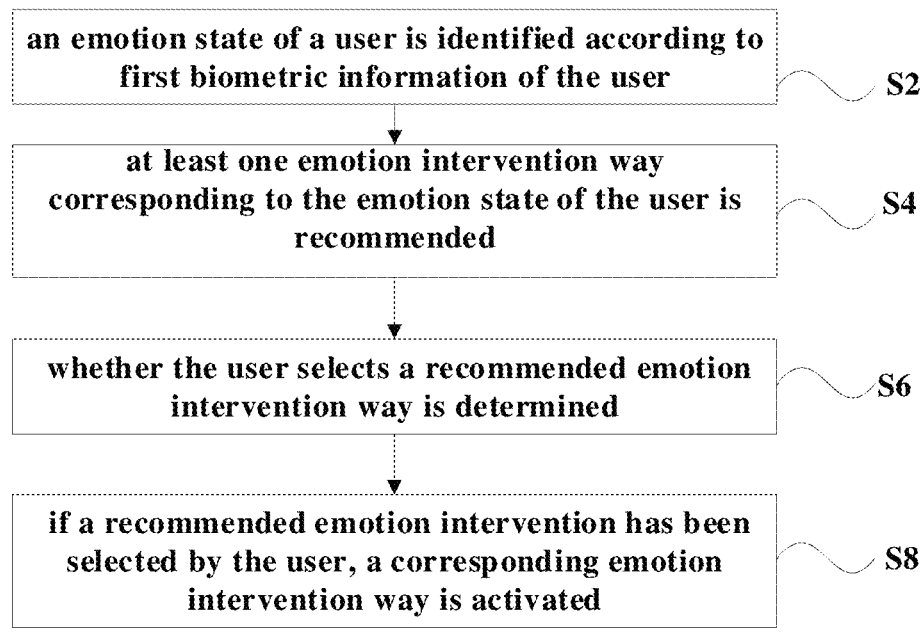
FIG. 1B is a flowchart illustrating an emotion intervention method according to another embodiment of the present disclosure.

FIG. 1B is a flowchart illustrating an emotion intervention method according to another embodiment of the present disclosure. FIG. 1B is different from FIG. 1A in that steps S6 and S8 are further comprised. Only the difference between FIG. 1B and FIG. 1A will be described below, and the same as in FIG. 1A will not be repeated.

As shown in FIG. 1B, in step S6, it is determined whether the user selects a recommended emotion intervention.

In step S8, if a recommended emotion intervention has been selected by the user, a corresponding emotion intervention is activated.

For example, if the user has selected an intervention of outputting media data, a corresponding display or player is activated according to the user's choice of picture or music, and a corresponding intervention picture or music will be randomly pushed.

For another example, if the user has selected physiotherapy, a physiotherapy device is activated, and the user is prompted to perform physiotherapy according to physiotherapy instructions.

If the user has selected an intervention of negative oxygen ions, a negative oxygen ion generator is activated and a timer is set to turn off the negative oxygen ion generator in time as needed. If the user has selected an aroma intervention, an aroma generator is activated. Of course, a timer can also be set at the same time to turn off the aroma generator at a predetermined time.

Figure 3:
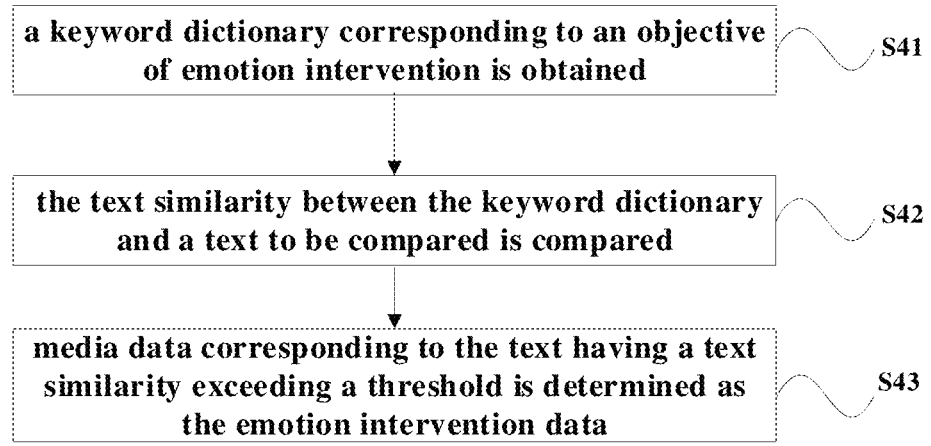
FIG. 3 is a flowchart illustrating a text similarity matching algorithm according to an embodiment of the present disclosure.

In some embodiments, the emotion intervention data is obtained through a text similarity matching algorithm. A text similarity matching algorithm according to some embodiments of the present disclosure will be described below with reference to FIG. 3. FIG. 3 is a flowchart illustrating a text similarity matching algorithm according to an embodiment of the present disclosure. As shown in FIG. 3, the text similarity matching algorithm comprises steps S41-S43.

In step S41, a keyword dictionary corresponding to an objective of emotion intervention is obtained.

The objective of emotion intervention is, for example, to ease the user's emotion. For example, if the emotion of the user is identified as angry, the objective of emotion intervention is to relieve the angry emotion. The keyword dictionary corresponding to the relief of the angry emotion comprises w keywords, wherein w is a positive integer. When the keywords are, for example, "soothing", "calm" and "cheerful", w is 3.

In some embodiments, these keywords may be expanded with similar words. For example, a semantic similarity matching algorithm is used to search for words similar to "cheerful", as a result words "happy" and "pleasant" may be found. The expanded keyword dictionary comprises "soothing", "calm", "cheerful", "happy" and "pleasant".

In step S42, the text similarity between the keyword dictionary and a text to be compared is compared.

The text to be compared is a collection of words, such as a text description or article about a picture, music, and video. For example, the text to be compared is "This music is cheerful, lively, and pleasant." The text to be compared can be directly obtained through web crawling. Alternatively, keywords in the keyword dictionary can be used to obtain the text to be compared through searching.

In order to facilitate comparison by a computer, a sparse algorithm can be used to convert the keyword dictionary and the text to be compared into binary codes, such as "01000001". The length and value of the code depend on the specific sparse algorithm.

Figure 4:
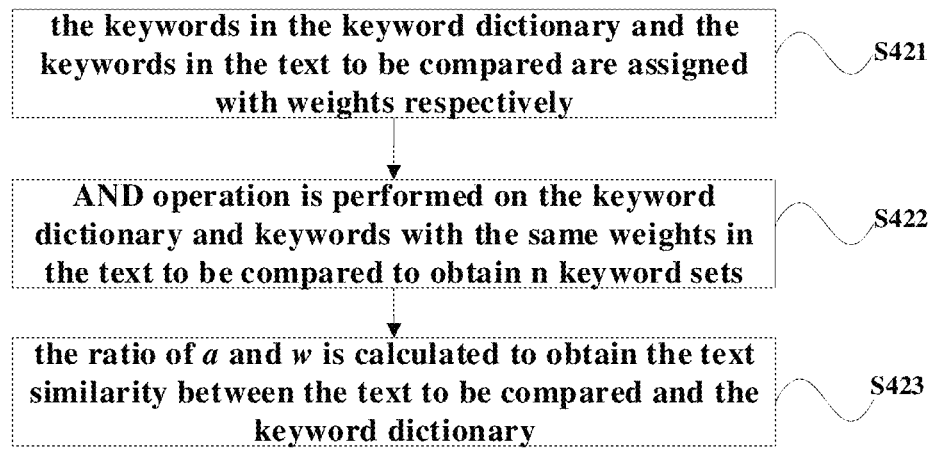
FIG. 4 is a flowchart illustrating a text similarity comparison method according to an embodiment of the present disclosure.

FIG. 4 is a flowchart illustrating a text similarity comparison method according to an embodiment of the present disclosure. As shown in FIG. 4, the text similarity comparison method comprises steps S421-S423.

In step S421, the keywords in the keyword dictionary and the keywords in the text to be compared are assigned with weights respectively. Weights reflect the importance of keywords. The keywords in the keyword dictionary have n weights, where n is a positive integer.

Still taking a keyword dictionary comprising "soothing", "calm", "cheerful", "happy" and "pleasant" as an example, a weight value of 4 can be assigned to "soothing" and "calm", and a weight value of 3 can be assigned to "cheerful", "happy", "pleasant". Therefore, the keyword dictionary has two weights, namely n=2. Similarly, in the comparison text "This music is cheerful, lively, and pleasant", the weights of the keywords "This", "music", "cheerful", "lively", "pleasant" may be 1, 2, 3, 3, 3, respectively.

In step S422, an AND operation is performed on the keyword dictionary and keywords with the same weights in the text to be compared to obtain n keyword sets. The n keyword sets comprise a keywords, where a is an integer.

In some embodiments, the text to be compared is searched for keywords with the same weights as in the keyword dictionary. In the above example, the keywords with the same weights are "cheerful", "lively", and "pleasant". By performing an AND operation on these keywords with the same weights, a keyword set comprising "cheerful", and "pleasant" can be obtained, that is, n=1.

Since the keyword dictionary has been expanded with similar words, similar words may be deleted from the keyword set obtained in step S422. That is, "pleasant" may be deleted from the keyword set, so that a=1.

In step S423, the ratio of a and w is calculated to obtain the text similarity between the text to be compared and the keyword dictionary.

According to the previous analysis, a/w=⅓. In some embodiments, the ratio of a to w can be used as the text similarity between the text to be compared and the keyword dictionary. Different keyword dictionaries have different w values. If "soothing" is not comprised in the keyword dictionary, we get w=2. Accordingly, it can be obtained that the text similarity between the text to be compared and the keyword dictionary is ½.

Returning to FIG. 3, how to determine the emotion intervention data after obtaining the text similarity between the user's text to be compared and the keyword dictionary will be described below.

In step S43, media data corresponding to the text having a text similarity exceeding a threshold are determined as the emotion intervention data.

Different thresholds can be set according to the actual situation. If the threshold is set to 45%, in the above example, for the case of w=2, the similarity obtained is 50%, media data (such as music) corresponding to the text to be compared can be determined as the emotion intervention data; and in the case of w=3, the obtained similarity is about 33%, so media data corresponding to the text to be compared is not determined as the emotion intervention data.

How to recommend an emotion intervention after acquiring the emotion intervention data will be described with a specific example below.

For example, if the emotion state of the user is sad, there are multiple emotion interventions available. For example, the user may be recommended to play cheerful music or positive pictures to motivate the user. Corresponding physiotherapy can also be recommended based on the correlation between the emotion state and physiotherapy. For example, massaging related acupoints can effectively relieve sadness. Certainly, it is also possible to recommend multiple emotion interventions at the same time to improve the effectiveness of the intervention.

To recommend an emotion intervention, second biometric information of the user may also be considered. The second biometric information comprises height, weight, health status and other information reflecting the user's physical state. The second biometric information may be obtained through an inquiry activity or the like. Information on height and weight can also be obtained through corresponding measurements.

In some embodiments, the physical state of the user is identified based on the second biometric information of the user; and at least one emotion intervention corresponding to the emotion state is recommended according to the physical state of the user. In this way, the recommended emotion intervention takes into account the user's physical state, and can more effectively interfere with the user's emotion.

For example, if the emotion state of the user is sad, cheerful music or positive pictures can be recommended to the user to motivate the user's emotion. However, if the user's eyes are uncomfortable, recommending cheerful music is easier to accept than positive pictures. Therefore, considering the user's physical state to recommend an emotional intervention will make emotional intervention more effective.

In some embodiments, a corresponding physiotherapy service is recommended according to the physical state of the user. For example, if the user's emotion state is identified as sad, but the user's eyes are uncomfortable, an eye physiotherapy service such as an eye massage can be recommended to the user. This is because the sadness of the user may be caused by the eye discomfort, and alleviating the eye discomfort can effectively reduce the sadness of the user.

As mentioned earlier, it is also possible to recommend multiple interventions to interfere with the user's emotion. For example, while recommending eye massage to the user, cheerful music can be recommended. On the one hand, alleviating the eye discomfort can effectively reduce the sadness of the user; on the other hand, cheerful music can also ease the sadness of the user. In this way, emotion intervention is more effective.

After obtaining the emotion intervention data, in addition to making emotion intervention recommendations, the obtained emotion intervention data can also be used to construct an emotion intervention repository.

Figure 5A:
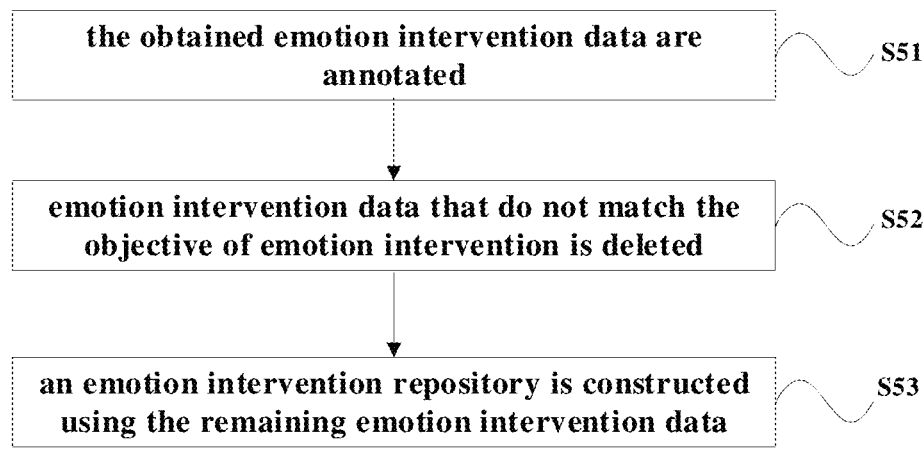
FIG. 5A is a flowchart illustrating a method for constructing an emotion intervention repository according to an embodiment of the present disclosure.

FIG. 5A is a flowchart illustrating a method for constructing an emotion intervention repository according to an embodiment of the present disclosure. As shown in FIG. 5A, the method for constructing an emotion intervention repository comprises steps S51-S53.

In step S51, the obtained emotion intervention data is annotated. For example, if the user's emotion is identified as angry, the objective of emotion intervention is to stabilize the emotion. For example, quiet pictures, text, audio, or video can be searched, and corresponding data obtained can be labeled as "stabilize emotion". Of course, it is also possible to annotate input emotion intervention data.

In step S52, emotion intervention data that does not match the objective of emotion intervention is deleted.

The obtained emotion intervention data may comprise data that does not match the objective of emotion intervention. For example, the data cannot stabilize the emotion. Thus, these data that do not match the objective of emotion intervention may be deleted.

In step S53, an emotion intervention repository is constructed using the remaining emotion intervention data. The emotion intervention repository comprises, but is not limited to, a picture repository, a music repository, a video repository, and a physiotherapy repository.

In some embodiments, after identifying the user's emotion state, the emotion intervention data is searched directly in the constructed emotion intervention repository. Based on such emotion intervention data, the recommended emotion intervention is more efficient.

Taking emotion intervention data that is a picture as an example, a method for constructing a picture repository through picture-based content searching according to some embodiments of the present disclosure will be described with reference to FIG. 5B. Constructing an image repository through picture-based content searching comprises: according to a hue of a background color of a picture and/or an object comprised in the picture, determining a content conformance degree of the picture; constructing a picture repository using pictures having content conformance degrees greater than or equal to a threshold.

Figure 5B:
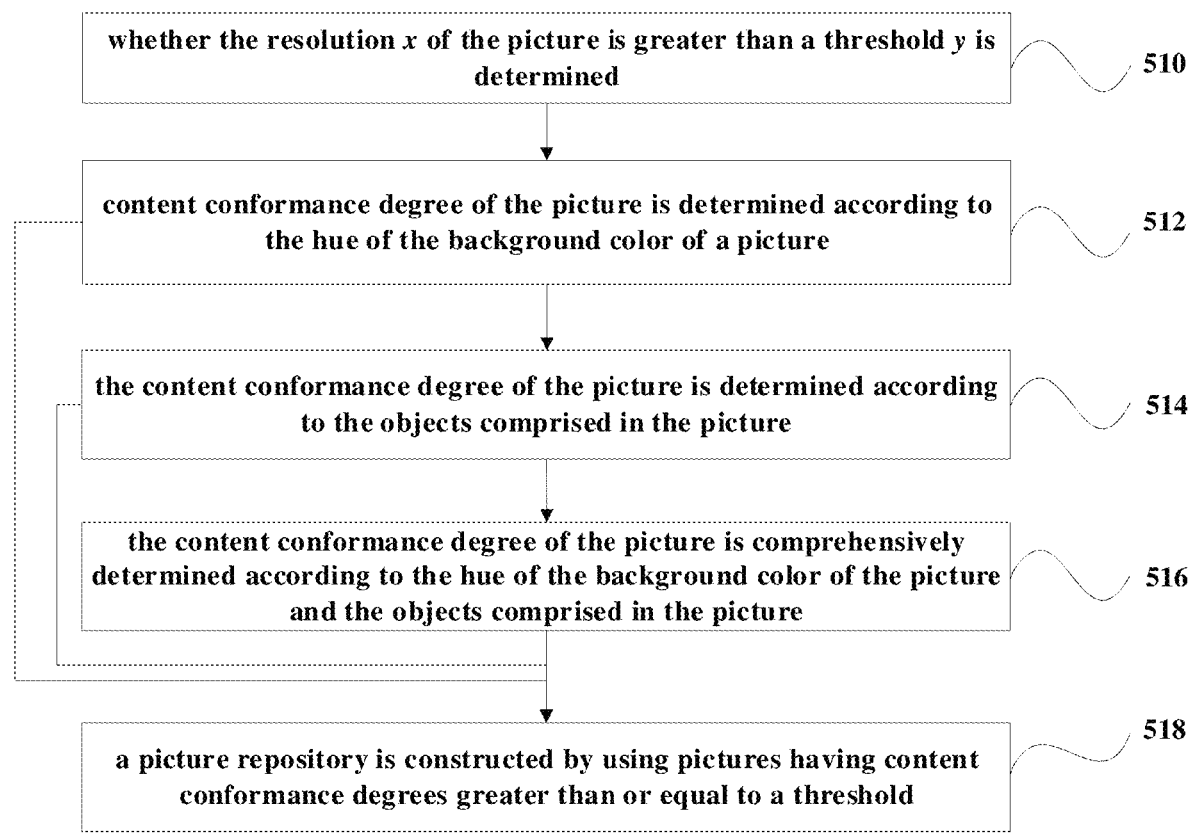
FIG. 5B is a flowchart illustrating a method for constructing a picture repository according to an embodiment of the present disclosure.

FIG. 5B is a flowchart illustrating a method for constructing a picture repository according to an embodiment of the present disclosure.

In step 512, according to the hue of the background color of a picture, a content conformance degree of the picture is determined.

According to the classification of the background color of a picture, it can be determined whether the background color of the picture is warm, neutral, or cool. For example, warm colors comprise red, orange, yellow, etc; neutral colors comprise purple, black, gray, white, etc; cool colors comprise green, cyan, blue, etc.

In some embodiments, pixel are counted according to the classification of the background color described above, that is, the number of pixels of warm colors can be counted as $n_1$, the number of pixels of neutral colors can be counted as $n_2$, and the number of pixels of cool colors can be counted as $n_3$; then, the percentages of warm color pixels, neutral color pixels, and cool color pixels in total pixels are computed according to the following formula (1)-(3), respectively:
the percentage of warm color pixels, $$color_1 = n_1/(n_1 + n_2 + n_3), \quad (1)$$

the percentage of neutral color pixels, $$color_2 = n_2/(n_1 + n_2 + n_3), \quad (2)$$

and the percentage of cool color pixels, $$color_3 = n_3/(n_1 + n_2 + n_3). \quad (3)$$

In general, if the background color of a picture belongs to warm or neutral hues, the content of the picture may be positive; otherwise, the content of the picture may be negative. That is, the probability that the content of the picture is positive can be determined according to the hue of the background color of the picture, that is, the content conformance degree of the picture can be determined. For example, a weighted sum of $color_1$, $color_2$, and $color_3$ can be used to reflect the content conformance degree of the picture.

Then, in step 518, a picture repository is constructed by using pictures with content conformance degrees greater than or equal to a threshold. That is, in a case where the content conformance degree of a picture is greater than or equal to the threshold, the corresponding picture is placed in the picture repository.

In other embodiments, whether the content of a picture is positive, neutral, or negative can also be determined based on the number of objects in the picture that correspond to positive, neutral, and negative emotions For example, pictures of positive emotions comprise objects that reflect victory, tourism and entertainment, beautiful scenery, flowers and trees, cute animals, pastimes, famous cars, banknotes, treasures, sports scenes, happy expressions, affection, friendship, love, etc; pictures of neutral emotions comprise objects that reflect daily necessities, life and work scenes, buildings, vehicles, diet, geometric figures, poker faces, etc; pictures of negative emotions comprise objects that reflect accidents, natural disasters, damage to objects (such as buildings), various garbage, ghosts, insects, medical treatment, corpses, environmental pollution, natural disasters, crying, disability, bloodshed, military scenes, violence and conflict, weapons, etc.

In step 514, according to the objects comprised in the picture, the content conformance degree of the picture is determined.

For example, according to the classification of the positive content, neutral content, and negative content in the pictures, the number of objects corresponding to positive emotions in the pictures is counted as $m_1$, the number of objects corresponding to neutral emotions is counted as $m_2$, and the number of objects corresponding to negative emotions is counted as $m_3$. Then, the percentages of positive emotion objects, neutral emotion objects, and negative emotion objects in the total objects in the picture can be computed according to the following formulas (4)-(6):

the percentage of positive emotion objects:
$$mod_1 = m_1/(m_1 + m_2 + m_3) \quad (4),$$

the percentage of neutral emotion objects, $mod_2 = m_2/(m_1 + m_2 + m_3)$ (5), and the percentage of negative emotion objects,
$$mod_3 = m_3/(m_1 + m_2 + m_3) \quad (6).$$

In general, if a picture comprises positive or neutral objects, the content of the picture may be positive; otherwise, the content of the picture may be negative. That is, the probability that the content of the picture is positive can be determined according to the objects comprised in the picture, that is, the content conformance degree of the picture can be determined. For example, a weighted sum of $mod_1$, $mod_2$, and $mod_3$ can be used to reflect the content conformance degree of the picture.

Then, in step 518, a picture repository is constructed by using pictures having content conformance degrees greater than or equal to a threshold. That is, in the case where the content conformance degree of a picture is greater than or equal to the threshold, the corresponding picture is placed in the picture repository.

It should be understood that the content conformance degree of the picture may be determined only according to step 512 or 514, that is, only steps 512 and 518 are performed, or only steps 514 and 518 are performed. Certainly, in order to determine the content conformance degree of the picture more accurately, the results of steps 512 and 514 can also be combined to determine the content conformance degree of the picture, that is, step 516 is performed.

In step 516, according to the hue of the background color of the picture and the objects comprised in the picture, the content conformance degree of the picture is comprehensively determined.

For example, the content conformance degree of the picture is computed according to the following formula (7):

$$f_1 = \gamma_1(\alpha_1 \cdot mod_1 + \alpha_2 \cdot mod_2 + \alpha_3 \cdot mod_3) + \gamma_2(\beta_1 \cdot color_1 + \beta_2 \cdot color_2 + \beta_3 \cdot color_3) \quad (7),$$

wherein, the values of $\alpha_1$, $\alpha_2$, $\alpha_3$, $\beta_1$, $\beta_2$, $\beta_3$, $\gamma_1$, $\gamma_2$ can be set according to actual needs. For example, $\alpha_1$ is 1, $\alpha_2$ is 0.5, $\alpha_3$ is −1; $\beta_1$ is 1, $\beta_2$ is 0.5, $\beta_3$ is −1; $\gamma_1$ is 0.5, $\gamma_2$ is 0.5.

Then, in step 518, a picture repository is constructed by using pictures having content conformance degrees greater than or equal to a threshold. That is, in the case where the content conformance degree of a picture is greater than or equal to the threshold, the corresponding picture is placed in the picture repository.

In some embodiments, in order to ensure that pictures in the constructed picture repository have at least a desired resolution, the pictures may also be filtered in advance. For example, in step 510, it is determined whether the resolution x of the picture is greater than a threshold y (that is, a desired resolution). Only if the resolution x of the picture is greater than y, the subsequent steps are performed.

Figure 5C:
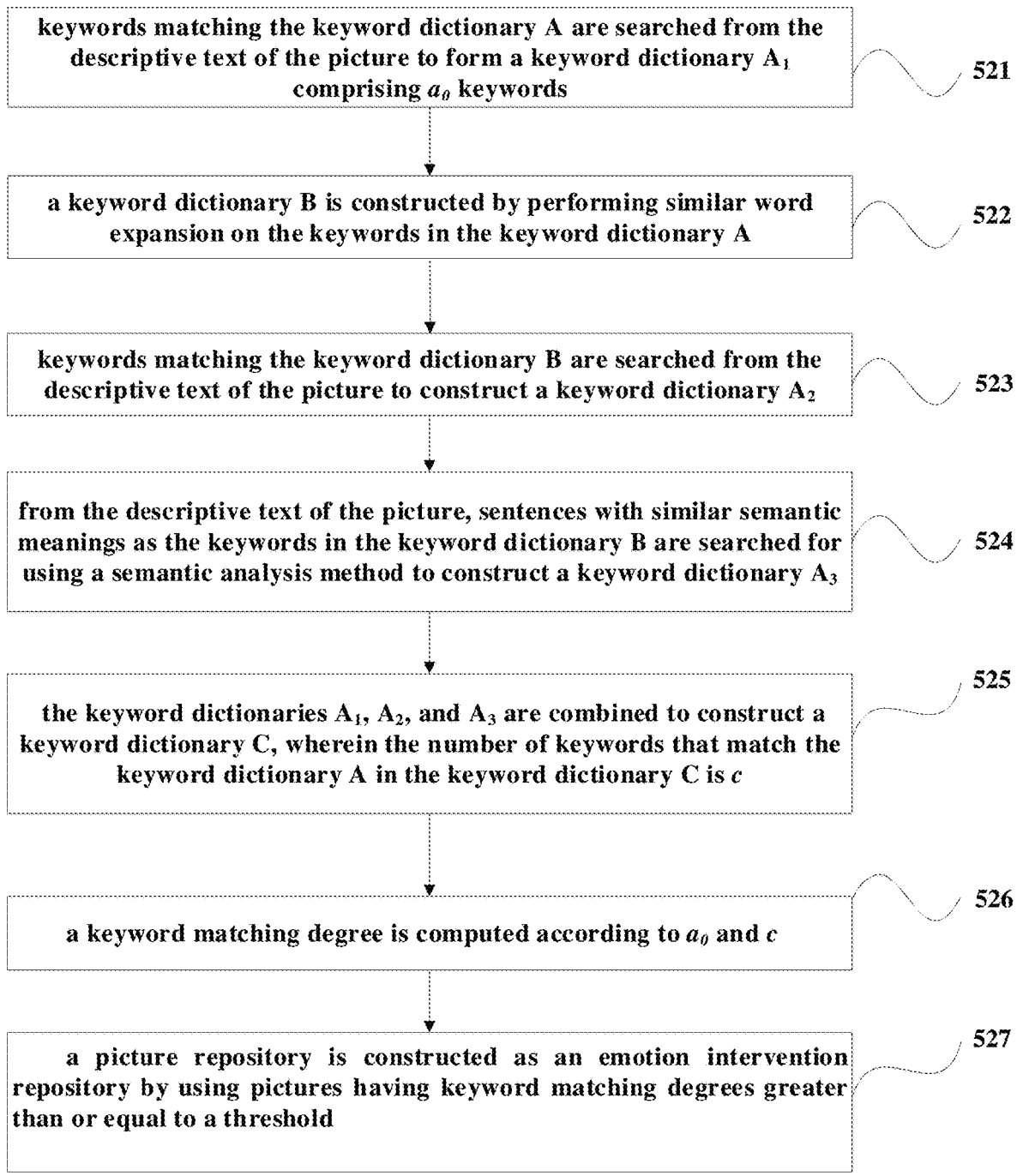
FIG. 5C is a flowchart illustrating a method for constructing a picture repository according to another embodiment of the present disclosure.

Taking emotion intervention data that is a picture as an example, a method for constructing a picture repository using a text-based natural language processing method according to some embodiments of the present disclosure will be described with reference to FIG. 5C. FIG. 5C is a flowchart illustrating a method for constructing a picture repository according to another embodiment of the present disclosure.

In step 521, keywords matching the keyword dictionary A are searched from the descriptive text of the picture to construct a keyword dictionary A1. The keyword dictionary A can be constructed using a text-based natural language processing method. The keyword dictionary A may be constructed in advance, or may be constructed before the execution of step 521. The keyword dictionary A comprises $a_0$ keywords, where $a_0$ is a positive integer. The number of keywords in the descriptive text of the picture that match the keyword dictionary A is $a_1$, where $a_1$ is a positive integer. These keywords construct a keyword dictionary $A_1$. Here, matched keywords comprise, for example, identical keywords, keywords having identical semantics, or keywords having similar semantics.

In step S522, a keyword dictionary B is constructed by performing similar word expansion for the keywords in the keyword dictionary A.

In step S523, keywords matching the keyword dictionary B are searched from the descriptive text of the picture to construct a keyword dictionary $A_2$. The number of keywords that are matched in the keyword dictionary B is $a_2$, where $a_2$ is a positive integer. These keywords form the keyword dictionary $A_2$.

In step S524, from the descriptive text of the picture, sentences with similar semantic meanings as the keywords in the keyword dictionary B are searched using a semantic analysis method to construct a keyword dictionary $A_3$. The number of keywords that are matched in the keyword dictionary B with the sentences having similar semantic meanings is $a_3$, where $a_3$ is a positive integer. These keywords form the keyword dictionary $A_3$.

In step 525, the keyword dictionaries $A_1$, $A_2$, and $A_3$ are combined to construct a keyword dictionary C. The number of keywords that match the keyword dictionary A in the keyword dictionary C is c, and c is a positive integer. For example, an AND operation can be performed on the keywords in the keyword dictionaries $A_1$, $A_2$, and $A_3$ to achieve the merging of the keyword dictionaries.

In step 526, a keyword matching degree is computed according to $a_0$ and c. For example, a keyword matching degree $f_2$ is computed: $f_2=c/a_0$.

In step 527, a picture repository is constructed as an emotion intervention repository by using pictures having keyword matching degrees greater than or equal to a threshold. That is, similar to step 518, if the content conformance degree of a picture is greater than or equal to the threshold, the corresponding picture is placed in the picture repository.

Figure 5D:
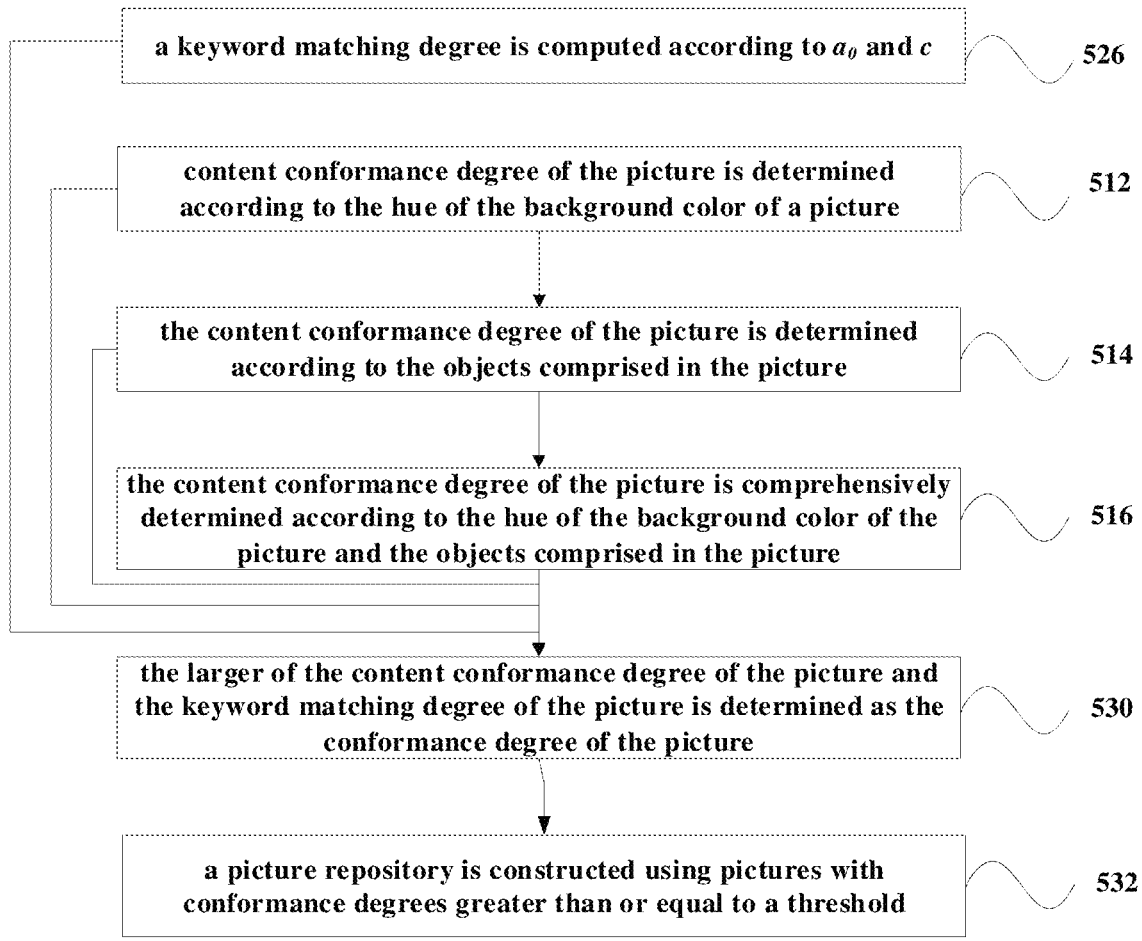
FIG. 5D is a flowchart illustrating a method for constructing a picture repository according to a further embodiment of the present disclosure.

In order to more accurately determine the content conformance degree of the picture, the results of FIGS. 5B and 5C can also be combined to construct the picture repository. A method for constructing a picture repository through picture-based content searching and text-based natural language processing according to some embodiments of the present disclosure will be described with reference to FIG. 5D. FIG. 5D is a flowchart illustrating a method for constructing a picture repository according to a further embodiment of the present disclosure.

In FIG. 5D, the results of step 516 in FIG. 5B and step 526 in FIG. 5C are used to construct a picture repository. As shown in FIG. 5D, after the content conformance degree f1 of the picture is obtained in step 516 and the keyword matching degree f2 of the picture is obtained in step 512, 514, or 516, the larger of the content conformance degree of the picture and the keyword matching degree of the picture can be determined as the conformance degree of the picture in step 530 using formula (8):

$$f=\max(f_1,f_2), \qquad (8)$$

In step 532, a picture repository is constructed using pictures with conformance degrees greater than or equal to a threshold. That is, in a case where the conformance degree of a picture, f, is greater than or equal to z, the corresponding picture is placed in the picture repository. Otherwise, the picture is discarded. In some embodiments, the picture may be manually calibrated before being placed in the picture repository.

In the above embodiment, the picture repository is constructed through picture-based content searching in combination with a text-based natural language processing method, so that the accuracy of picture matching can be improved.

Figure 6:
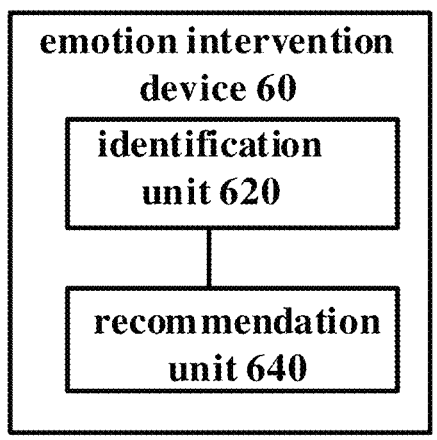
FIG. 6 is a block diagram illustrating an emotion intervention device according to an embodiment of the present disclosure.

FIG. 6 is a block diagram illustrating an emotion intervention device according to an embodiment of the present disclosure. As shown in FIG. 6, the emotion intervention device 60 comprises an identification unit 620 and a recommendation unit 640.

The identification unit 620 is configured to, for example, perform step S2 shown in FIG. 1. As described above, a facial expression of the user can be obtained through an image sensor, and then an emotion state of the user can be identified according to the correlation between the facial expression and the emotion state.

The recommendation unit 640 is configured to, for example, perform step S4 shown in FIG. 1. As described above, corresponding emotion intervention data can be obtained based on the user's emotion state, and at least one emotion intervention corresponding to the emotion state can be selected therefrom. In some embodiments, an emotion intervention is recommended through comprehensively considering the user's emotion state and physical state.

Figure 7:
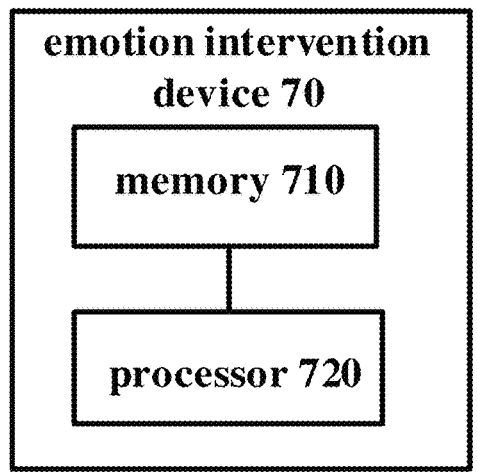
FIG. 7 is a block diagram illustrating an emotion intervention device according to another embodiment of the present disclosure.

FIG. 7 is a block diagram illustrating an emotion intervention device according to another embodiment of the present disclosure.

As shown in FIG. 7, the emotion intervention device 70 comprises a memory 710 and a processor 720 coupled to the memory 710. The memory 710 is configured to store instructions for executing a corresponding embodiment of the emotion intervention method. The processor 720 is configured to execute the emotion intervention method in any of the embodiments of the present disclosure based on the instructions stored in the memory 710.

It should be understood that each step in the foregoing emotion intervention method may be implemented by a processor, and may be implemented in any of software, hardware, firmware, or a combination thereof.

In addition to the emotion intervention method and device, an embodiment of the present disclosure may also take the form of a computer program product implemented on one or more non-volatile storage media containing computer program instructions. Therefore, an embodiment of the present disclosure also provides a computer-readable storage medium having computer instructions stored thereon, which when executed by a processor implement the emotion intervention method in any of the foregoing embodiments.

An embodiment of the present disclosure further provides an emotion intervention system, comprising the emotion intervention device according to any of the foregoing embodiments.

Figure 8:
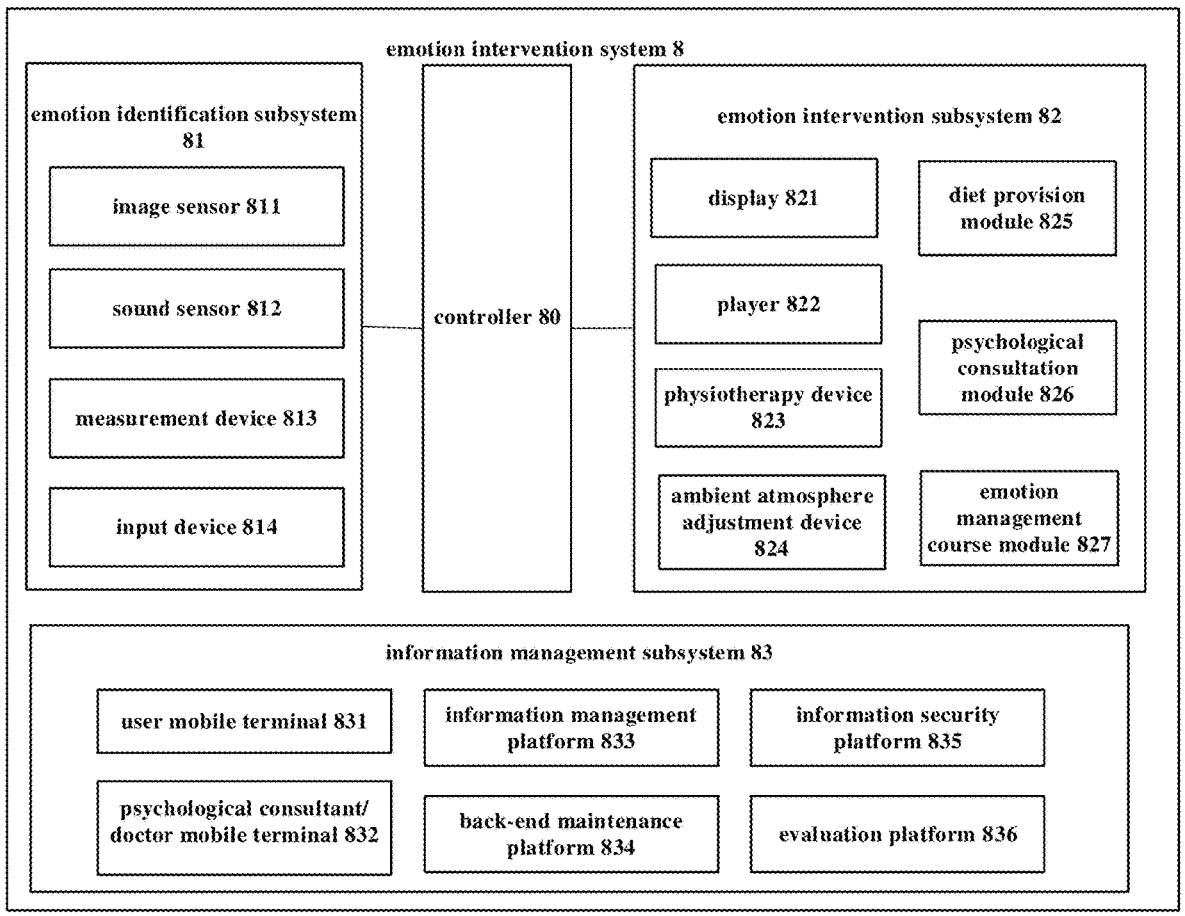
FIG. 8 is a block diagram illustrating an emotion intervention system according to an embodiment of the present disclosure.

FIG. 8 is a block diagram illustrating the emotion intervention system according to an embodiment of the present disclosure.

As shown in FIG. 8, the emotion intervention system 8 comprises a controller 80, an emotion identification subsystem 81, and an emotion intervention subsystem 82. The controller 80 is configured to perform the emotion intervention method described in any of the foregoing embodiments. The structure of the controller 80 may be similar to the emotion intervention device 60 or 70 described above.

The emotion identification subsystem 81 is configured to identify a user's emotion. In some embodiments, the emotion identification subsystem 81 comprises at least one of an image sensor 811, a sound sensor 812, a measurement device 813, or an input device 814.

The image sensor 811 is configured to obtain first biometric information of a user. For example, the user's image may be captured by a camera or the like. As described above, a facial expression of the user can be obtained as the user's first biometric information through analyzing facial features in the user's image.

In some embodiments, the image sensor 811 may also be configured to obtain second biometric information of the user. For example, the height of the user may be computed as the user's second biometric information based on the user's whole body image and the size of a reference object in the image.

The sound sensor 812 is configured to obtain the first biometric information of the user. For example, the user's voice may be sensed through a microphone or the like as the user's first biometric information.

The measurement device 813 is configured to obtain the second biometric information of the user. For example, the height of the user may be measured by a scale, and the weight of the user may be measured by a weight scale.

The input device 814 is configured to obtain the second biometric information of the user. As described above, the second biometric information of the user may be obtained through inquiry. That is, the user can input second biometric information such as height, weight, and health status through text input and the like. In some embodiments, the user may also directly input his or her emotion perception through an input device. In some embodiments, more detailed and accurate second biometric information of the user may be obtained by entering the user's medical case, etc.

The emotion intervention subsystem 82 is configured to interfere with the user's emotion. In some embodiments, the emotion intervention subsystem 82 comprises at least one of a display 821, a player 822, a physiotherapy device 823, or an ambient atmosphere adjustment device 824.

The display 821 and the player 822 are configured to output media data if the recommended emotion intervention comprises output of media data.

The display 821 may also be configured to display data such as text or pictures input by the user. In some embodiments, the display comprises a LCD or an OLED (Organic Light-Emitting Diode) display. The display may be any product or component having a display function, such as a mobile phone, a tablet computer, a television, a notebook computer, a digital photo frame, a navigator, a projection screen, etc. In addition to the conventional two-dimensional display, it may also be a virtual reality (VR), augmented reality (AR), or holographic projection device.

In addition to playing audio for emotion intervention, the player 822 may be configured to play a voice input by the user. The player is, for example, a speaker or a headset.

The physiotherapy device 823 is configured to perform physiotherapy on the user if the recommended emotion intervention comprises physiotherapy. Depending on the recommended physiotherapy, such as massage, phototherapy, magnetic therapy, different physiotherapy devices can be used. The physiotherapy device can be activated via a wireless Bluetooth connection or a wired connection. In some embodiments, the physiotherapy device is a massage chair.

The ambient atmosphere adjustment device 824 is configured to provide a negative oxygen ion environment or a designated lighting environment if the recommended mood intervention comprises ambient atmosphere adjustment. The environmental atmosphere adjustment device 824 may provide different negative oxygen ion environment or different lighting environment effects according to needs. For example, the ambient atmosphere adjustment device 824 comprises a negative oxygen ion generator and a negative oxygen ion controller, or a light generator (i.e., a light source) and a light controller.

In other embodiments, the ambient atmosphere adjustment device 824 is configured to be a device capable of emotion intervention through supplying a floral fragrance, a grass fragrance, and the like. For example, the ambient atmosphere adjustment device 824 comprises various fragrance generators and controllers.

In still other embodiments, the ambient atmosphere adjustment device 824 further comprises a light sensor, a temperature sensor, or a humidity sensor, so as to adjust the light, temperature, or humidity of the environment as required.

In some embodiments, the ambient atmosphere adjustment device 824 may further comprise auxiliary devices such as a timer and a squeaker, so as to periodically switch the corresponding device on or off as needed to achieve a desired ambient atmosphere.

In some embodiments, the emotion intervention subsystem 82 may further comprise: a diet provision module 825 configured to provide a corresponding diet if the recommended emotion intervention comprises provision of diet, so as to stimulate the user's nerves system from the sense of taste to achieve the purpose of emotion intervention. The diet provision module 825 may comprise a commodity storage machine, an online payment system, a supply channel, a wireless transceiver module, and the like. The diet provision module 825 is, for example, a vending machine.

In some embodiments, the emotion intervention subsystem 82 further comprises a psychological consultation module 826 configured to provide an online psychological consultation referral appointment service if the recommended emotion intervention method comprises provision of psychological consultation. The psychological consultation module 826 is configured to evaluate the user's mental health using big data modeling in accordance with the user's emotion state, and to provide a psychological self-referral appointment service for a user whose evaluation result is at high risk of mental imbalance, to achieve emotion health management.

In other embodiments, the emotion intervention subsystem further comprises: an emotion management course module 827 configured to provide an emotion management course such as an online psychological management course if the recommended emotion intervention comprises provision of emotion management courses. The courses comprise parent-child courses, intimacy courses, emotion quotient courses, adversity quotient courses, social courses, etc. The courses may take the form of video courses, e-book courses, etc. The courses can be displayed and played on a monitor.

In some embodiments, the emotion intervention system 8 may further comprise an information management subsystem 83. In some embodiments, the information management subsystem 83 comprises a user mobile terminal 831, a psychological consultant/doctor mobile terminal 832, an information management platform 833, a back-end maintenance platform 834, an information security platform 835, an evaluation platform 836, etc.

The user mobile terminal 831 has a registration and login module, an online appointment module, an online psychological evaluation module, an online course viewing module, an online social module, a consultation service module, and a personal information management module.

The registration and login module comprises two functions of registration and login. The online appointment module comprises an online experience store appointment function, an online intervention package appointment function, an online psychological counselor appointment function, an online doctor appointment function, an online course appointment function, etc. The online psychological evaluation module comprises an online evaluation function that is mainly based on psychological scaling and supplemented by other online evaluation methods. The online course viewing module comprises functions for viewing courses online, such as viewing course categories, course list, course details, course playback, course search, etc. The online social module comprises social functions mainly for online Tieba communication and social network groups. The consultation service module comprises the functions of customer contact and consulting service. The personal information management module comprises functions such as managing personal information, member information, system messages, appointment information, message push, cache clearing, and logging out.

The psychological consultant/doctor mobile terminal 832 comprises a registration login-qualification verification module, an appointment information viewing module, a schedule information viewing module, a message notification module, and a system setting module.

The registration login-qualification verification module comprises a psychological consultant/doctor registration function, a psychological consultant/doctor login function, and a psychological consultant/doctor qualification verification function. The appointment information viewing module comprises functions for viewing appointment details such as the person who made the appointment, the appointment time, and the appointment place. The message notification module comprises functions such as notification of new appointment, notification of cancellation of appointment, and timing notification of all appointment information. The system setting module comprises functions such as setting the appointment time, weekly setting, time period setting, and adjusting account status.

The information management platform 833 comprises a user management module, a psychological consultant/doctor management module, an appointment management module, a social management module, a course management module, a promotion management module, an experience store management module, a setting module, a payment module, an online customer service module, and a message push module, etc.

The user management module comprises functions such as user registration and login management, registered user statistics, member statistics, and member payment data statistics. The user management module may further comprise a function for a member manager to manage member information. The consultant/doctor management module comprises consultant account, consultant introduction and maintenance functions.

The appointment management module comprises functions of emotion intervention package appointment and psychological consultation package management. The appointment management module may further comprise functions such as experience store appointment statistics, consultant appointment statistics, doctor appointment statistics, and intervention package appointment statistics.

The social management module comprises functions such as social information management and maintenance, and is used to provide a communication platform between members or between members and a manager. Advertisements on the platform are grouped according to information such as members' companies, industries and home addresses, which can allow members to integrate into their work and living communities more quickly, and learn more about the information about their work and living communities, facilitating the solving of problems.

The course management module comprises course list, course details, course release and other functions. The promotion management module comprises functions such as coupon type, coupon usage statistics, creation of coupon usage rules, creation of coupon quota, creation of coupon validity, and coupon user selection. The experience store management module comprises functions such as experience store information maintenance and experience store administrator management, etc.

The setting module comprises functions such as carousel configuration, role management, administrator account and permission configuration, message push, and system log, etc. The payment module is used to pay for emotion healing package fees, membership fees, beverage costs, course fees, and psychological consultation fees. The message push module is used to push messages such as WeChat messages.

The back-end maintenance platform 834 comprises a picture and music repository update module, a course update module, an expert annotation module, and a maintenance login module.

The picture and music repository update module is used to update the picture repository and the music repository in the healing repository. The course update module is used to update the contents of the courses. The expert annotation module is used to annotate pictures and music automatically searched from the network, and pictures and music manually added. The maintenance and login module is used to maintain the login system, the back-end database, and the administrator system, comprising picture and music repository update, course update, administrator management and maintenance, member information maintenance, psychological consultant information management and maintenance, and doctor information management and maintenance functions. The information security platform is used to ensure the information security of the overall system.

The evaluation platform 835 is used for service quality and system evaluation, and comprises a service evaluation portion and a feedback portion. Service evaluation comprises three aspects: environmental experience evaluation, service experience evaluation, and system experience evaluation. Experience evaluation results are fed back to the system to update the system. The evaluation platform can also analyze the status of a group of users based on their recorded utilization frequency, the time of last login, and the total amount of consumption. For example, a customer model can be used to analyze key members, key developing members, key members to be kept, key members to be retained, general members, general developing members, general members to be kept, general members to be retained, and provide early warning of customer loss.

The emotion intervention system provided by the embodiment of the present disclosure can be installed in various places, for example, in an open, semi-open, or closed environment, such as a clinic, a shopping mall, or the like. For example, it can be installed in a closed room with a door in order to further control the temperature of the environment or the content of negative oxygen ions, that is, to form a healing room that can perform emotional intervention.

Figure 9A:
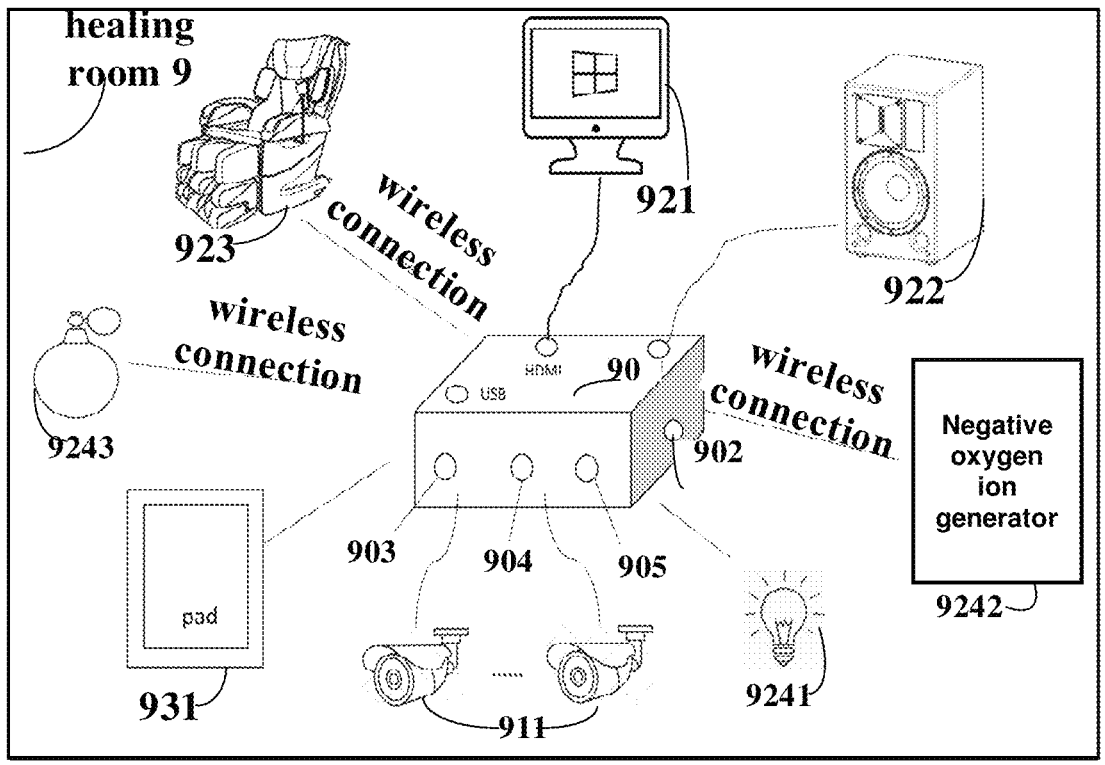
FIG. 9A is a schematic structural diagram illustrating a healing room according to an embodiment of the present disclosure.

FIG. 9A is a schematic structural diagram illustrating a healing room according to an embodiment of the present disclosure. In some embodiments, the healing room 9 comprises an emotion identification subsystem. As shown in FIG. 9A, the emotion identification subsystem is located in a black box 90. The structure of the emotion identification subsystem is similar to the emotion identification subsystem 81 of FIG. 8. For example, it is provided with an image sensor to capture a user's image. As shown in FIG. 9A, the black box 90 is provided with a plurality of cameras 911. As described above, facial feature analysis can be performed on the user's image to obtain a facial expression of the user, thereby identifying the emotion state of the user.

As shown in FIG. 9A, the healing room 9 further comprises an emotion intervention subsystem. The structure of the emotion intervention subsystem is similar to the emotion intervention subsystem 82 of FIG. 8. For example, it comprises a display 921, a player 922, a massage chair 923, and a light source 9241, a negative oxygen ion generator 9242, an aroma generator 9243, and other ambient atmosphere adjustment devices.

The healing room 9 further comprises an information management subsystem. The structure of the information management subsystem is similar to the information management subsystem 83 of FIG. 8, and comprises a user mobile terminal such as a tablet computer 931.

The black box 90 may further comprise some components of the emotion intervention subsystem and the information management subsystem. For example, an ambient atmosphere adjustment device such as a timer or an aroma controller may be provided in the black box 90. As another example, a back-end maintenance platform such as a picture and music repository update module, a course update module, and an expert annotation module may be provided in the black box. Of course, a controller for controlling the emotion intervention system can also be provided in the black box.

As shown in FIG. 9A, various interfaces are provided on the black box 90 for connection with external devices. The interfaces comprise, for example, a USB interface, an HDMI interface, an audio interface 901, a power interface 902, etc. The display 921, player 922, massage chair 923, and light source 9241, negative oxygen ion generator 9242, aroma generator 9243, tablet computer 931 described above can be wirelessly connected to the black box 90. Correspondingly, the black box 90 may be provided with corresponding wireless transceiver modules, such as a Bluetooth module, a WIFI module, and a 3G/4G/5G module. Of course, the connections can also be wired connections.

In some embodiments, as shown in FIG. 9A, the black box 90 is further provided with keys such as an On/Off key 903, volume keys 904, and a reset key 905, so that the user can perform operations as required. A touch screen may be provided on the top surface of the black box 90 for user operation.

In the healing room of some embodiments, the user's face image is collected in real time through a camera to identify the user's emotion state. For negative emotions that are not conducive to the user's health, a "six-in-one" method can be taken to intervene in the negative emotions of user in the sense of acoustics (such as music) and vision (such as pictures), tactile (such as physiotherapy), smell (such as aroma), taste (such as drinks), and environment (such as negative oxygen ions). The healing room can be used for psychologically sub-healthy people of all ages. It has the functions of emotion identification and emotion intervention, and can be used in various scenarios such as communities, families and business places.

Figure 9B:
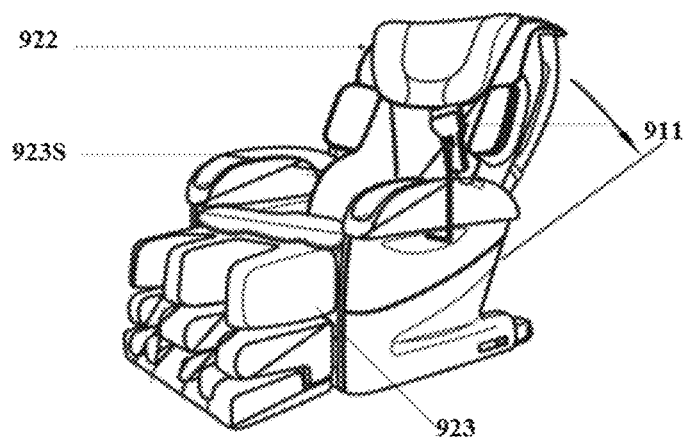
FIG. 9B is a schematic structural diagram illustrating a massage chair according to an embodiment of the present disclosure.

FIG. 9B is a schematic structural diagram illustrating a massage chair according to an embodiment of the present disclosure.

As shown in FIG. 9B, an image sensor 911 such as a camera is mounted on the massage chair 923. The massage chair 923 is also equipped with a player 922, such as a stereo or a headset. In some embodiments, the massage chair may be equipped with a sound sensor, such as a microphone. Users can enter voice messages through the microphone. The massage chair can also be equipped with measuring equipment, such as a scale to measure height.

As shown in FIG. 9B, the massage chair 923 is further provided with adjustment switches 923S, which are used to adjust the angle of the massage chair, the massage strength of the massage chair, and the stretching strength.

Figure 10:
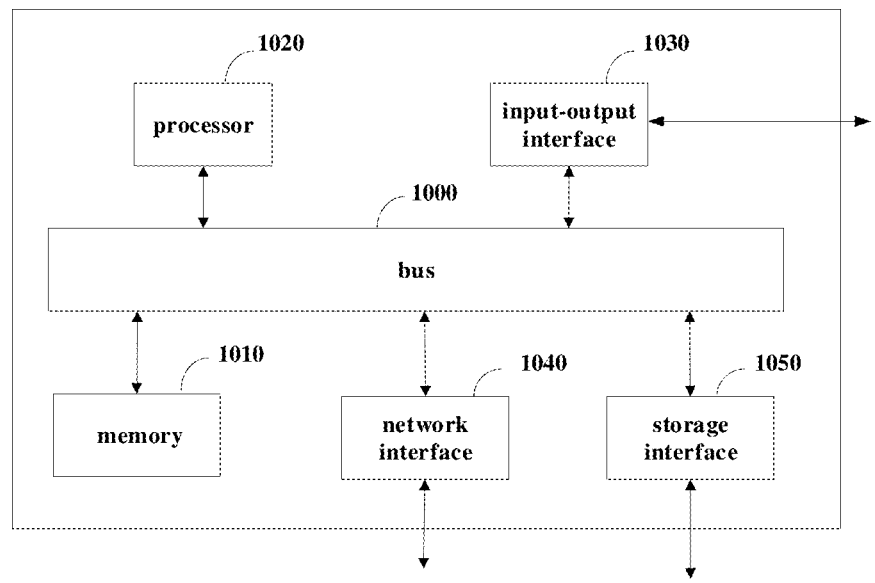
FIG. 10 is a block diagram illustrating a computer system for implementing an embodiment of the present disclosure.

FIG. 10 is a block diagram illustrating a computer system for implementing an embodiment of the present disclosure.

As shown in FIG. 10, the computer system can be represented in the form of a general-purpose computing device. The computer system comprises a memory 1010, a processor 1020, and a bus 1000 connecting different system components.

The memory 1010 may comprise, for example, a system memory, a non-volatile storage medium, and the like. The system memory stores, for example, an operating system, application programs, a boot loader (Boot Loader), and other programs. The system memory may comprise a volatile storage medium such as random access memory (RAM) and/or cache memory. The non-volatile storage medium stores, for example, instructions for executing a corresponding embodiment of the display method. The non-volatile storage medium comprises, but not limited to, magnetic disk storage, optical storage, flash memory, and the like.

The processor 620 may be implemented by a central processing unit (CPU), a digital signal processor (DSP), an application specific integrated circuit (ASIC), a field programmable gate array (FPGA) or other programmable logic devices, or discrete hardware components such as discrete gates or transistors. Accordingly, each device such as the judgment device and the determination device may be implemented by a central processing unit (CPU) running instructions that execute the corresponding steps, or may be implemented by a dedicated circuit that executes the corresponding steps.

The bus 1000 may has any of a variety of bus structures. For example, these structures comprise, but are not limited to, an Industry Standard Architecture (ISA) bus, a Micro Channel Architecture (MAC) bus, and peripheral component interconnects (PCI) bus.

The computer system may further comprise an input-output interface 1030, a network interface 1040, a storage interface 1050, and the like. These interfaces 1030, 1040, 1050, the memory 1010 and the processor 1020 may be connected through a bus 1000. The input/output interface 1030 may provide a connection interface for input/output devices such as a display, a mouse, and a keyboard. The network interface 1040 provides a connection interface for various networked devices. The storage interface 1050 provides a connection interface for external storage devices such as a floppy disk, a flash disk, or an SD card.

Heretofore, various embodiments of the present disclosure have been described in detail. In order to avoid obscuring the concepts of the present disclosure, some details known in the art are not described. Based on the above description, those skilled in the art can understand how to implement the technical solutions disclosed herein.

Although some specific embodiments of the present disclosure have been described in detail by way of example, those skilled in the art should understand that the above examples are only for the purpose of illustration and are not intended to limit the scope of the present disclosure. It should be understood by those skilled in the art that the above embodiments may be modified or equivalently substituted for part of the technical features without departing from the scope and spirit of the present disclosure. The scope of the disclosure is defined by the following claims.

What is claimed is:

1. An emotion intervention method, comprising:
   identifying an emotion state of a user according to first biometric information of the user;
   recommending at least one emotion intervention way corresponding to the emotion state, comprising
   obtaining emotion intervention data corresponding to the emotion state of the user, the intervention data comprising at least one of a physiotherapy suggestion or media data, and
   recommending at least one emotion intervention way corresponding to the emotion state based on the obtained emotion intervention data;
   annotating the obtained emotion intervention data, deleting emotion intervention data that do not match an objective of emotion intervention, and constructing an emotion intervention repository using the remaining emotion intervention data; or
   determining whether the recommended emotion intervention way has been chosen by the user, and if the recommended emotion intervention way has been chosen by the user, activating a corresponding emotion intervention.

2. The emotion intervention method according to claim 1, wherein the at least one emotion intervention way corresponding to the emotion state is recommended according to second biometric information of the user.

3. The emotion intervention method according to claim 2, wherein recommending at least one emotion intervention way corresponding to the emotion state comprises:
   identifying a physical state of the user based on the second biometric information of the user; and
   recommending the at least one emotion intervention way corresponding to the emotion state according to the physical state of the user.

4. The emotion intervention method according to claim 3, wherein:
   the first biometric information comprises at least one of a facial expression or a sound; and
   the second biometric information comprises at least one of a height, a weight, or a health condition.

5. The emotion intervention method according to claim 1, the emotion intervention way comprises at least one of output of media data, adjustment of ambient atmosphere, provision of diet, provision of psychological consultation, provision of emotion management courses, or physiotherapy.

6. The emotion intervention method according to claim 1, wherein identifying an emotion state of the user comprises:
   obtaining first biometric information of the user in real time;
   determining real-time emotion states of the user based on the first biometric information obtained in real time;
   counting proportions of each of the real-time emotion states of the user in a unit time; and
   identifying a real-time emotion state with the largest proportion as the emotion state of the user in the unit time.

7. The emotion intervention method according to claim 1, wherein obtaining first biometric information of the user comprises:
   obtaining an image of the user;
   identifying a face of the user from the image;
   identifying a facial expression of the user according to features of the face; and
   using the identified facial expression as the first biometric information.

8. The emotion intervention method according to claim 1, wherein the emotion intervention data are obtained by a text similarity matching algorithm.

9. The emotion intervention method according to claim 8, wherein obtaining the emotion intervention data through a text similarity matching algorithm comprises:
   obtaining a keyword dictionary corresponding to an objective of emotion intervention, wherein the keyword dictionary comprises w keywords, where w is a positive integer;
   comparing the text similarity between the keyword dictionary and a text to be compared; and
   determining media data corresponding to a text with a text similarity exceeding a similarity threshold as the emotion intervention data.

10. The emotion intervention method according to claim 9, wherein comparing the text similarity between the keyword dictionary and a text to be compared comprises:
    assigning weights to the keywords in the keyword dictionary and keywords in the text to be compared, respectively, wherein the weights reflect importance of the keywords, and the keywords in the keyword dictionary have n weights, where n is a positive integer;
    performing an AND operation on the keywords in the keyword dictionary and the keywords in the text to be compared that have the same weights to obtain n keyword sets, wherein the n keyword sets comprise a keywords, where a is an integer; and
    computing a ratio of a and w to obtain a text similarity between the text to be compared and the keyword dictionary.

11. The emotion intervention method according to claim 9, wherein the text to be compared is obtained by searching with keywords in the keyword dictionary.

12. An emotion intervention device, comprising:
    memory; and a processor coupled to the memory and configured to carry out the emotion intervention method according to claim 1, based on instructions stored in the memory.

13. An emotion intervention system, comprising:

the emotion intervention device according to claim 12; and at least one of a physiotherapy device, an ambient atmosphere adjustment device, a display, a player, a diet provision module, a psychological consultation module, an emotion management course module, an image sensor, a sound sensor, a measurement device, or an input device, wherein:

the physiotherapy device is configured to, if the recommended emotion intervention comprises physiotherapy, perform physiotherapy on the user;

the ambient atmosphere adjustment device is configured to, if the recommended emotion intervention comprises an ambient atmosphere adjustment, perform the ambient atmosphere adjustment;

the display and the player are configured to, if the recommended emotion intervention comprises output of media data, output the media data;

the diet provision module is configured to, if the recommended emotion intervention comprises provision of diet, provide a corresponding diet so as to stimulate nervous system of the user from a sense of taste;

the psychological consultation module is configured to, if the recommended emotion intervention comprises provision of psychological consultation, provide an online psychological consultation referral appointment service;

the emotion management course module is configured to, if the recommended emotion intervention comprises provision of emotion management courses, provide emotion management courses such as online psychological management courses;

the image sensor and the sound sensor are configured to obtain the first biometric information of user; and the measurement device and the input device are configured to obtain the second biometric information of the user.

14. The emotion intervention system according to claim 13, wherein the physiotherapy device comprises a massage chair.

15. A non-transient computer-readable storage medium on which a computer program is stored, which when executed by a processor implements the emotion intervention method according to claim 1.

16. An emotion intervention method comprising:

identifying an emotion state of a user according to first biometric information of the user;

recommending at least one emotion intervention way corresponding to the emotion state;

according to a hue of a background color of a picture and/or an object comprised in the picture, determining a content conformance degree of the picture;

constructing a picture repository as an emotion intervention repository by using pictures having content conformance degrees greater than or equal to a first threshold; and activating a corresponding emotion intervention according to the emotion invention repository.

17. An emotion intervention device, comprising:

memory; and a processor coupled to the memory and configured to carry out the emotion intervention method according to claim 16, based on instructions stored in the memory.

18. A non-transient computer-readable storage medium on which a computer program is stored, which when executed by a processor implements the emotion intervention method according to claim 16.

19. An emotion intervention method comprising:

identifying an emotion state of a user according to first biometric information of the user;

recommending at least one emotion intervention way corresponding to the emotion state;

searching for keywords matching a keyword dictionary A from the descriptive text of a picture, wherein the keyword dictionary A comprises $\alpha_0$ keywords, $\alpha_0$ being a positive integer, and the keywords matched in the keyword dictionary A forming a keyword dictionary $A_1$;

performing similar word expansion on keywords in the keyword dictionary A to construct a keyword dictionary B;

searching for keywords matching the keyword dictionary B from the descriptive text of the picture, wherein the keywords matched in the keyword dictionary B constitute a keyword dictionary $A_2$;

from the descriptive text of the picture, searching for a sentence with a similar semantic to the keywords in the keyword dictionary B using a semantic analysis method, wherein keywords in the searched semantically similar sentence that match the keyword dictionary B constitute a keyword dictionary $A_3$;

combining the keyword dictionaries $A_1$, $A_2$, and $A_3$ to constitute a keyword dictionary C, wherein the number of keywords in the keyword dictionary C that match the keyword dictionary A is c, where c is a positive integer;

computing a keyword matching degree based on $\alpha_0$ and c;

constructing a picture repository using pictures having keyword matching degrees greater than or equal to a second threshold, as an emotion intervention repository; and activating a corresponding emotion intervention according to the emotion invention repository.

20. The emotion intervention method according to claim 19, further comprising:

determining a larger value of the content matching degree and the keyword matching degree of the picture as the conformance degree of the picture; and constructing a picture repository as an emotion intervention repository using pictures that have conformance degrees greater than or equal to a third threshold.

\* \* \* \* \*